United States Patent [19]

Fisher, Jr.

[11] 4,178,930

[45] Dec. 18, 1979

[54] COMBINED CAP AND NEEDLE STRUCTURE

[76] Inventor: Frank R. Fisher, Jr., 9614 N. Charlotte Ave., Kansas City, Mo. 64155

[21] Appl. No.: 847,158

[22] Filed: Oct. 31, 1977

[51] Int. Cl.² .............................................. A61M 5/00
[52] U.S. Cl. ........................... 128/215; 128/218 NV; 128/221
[58] Field of Search ................. 128/221, 215, 218 N, 128/218 NV, 218 R, 218 DA, 220, 216

[56] References Cited

U.S. PATENT DOCUMENTS

| | | | |
|---|---|---|---|
| 3,368,557 | 2/1968 | Hassing et al. | 128/221 |
| 3,406,686 | 10/1968 | Keller | 128/218 NV |
| 3,413,974 | 12/1968 | Cohen | 128/218 NV |
| 3,739,779 | 6/1973 | Pfleger | 128/218 DA |
| 3,820,652 | 6/1974 | Thackston | 128/218 NV |
| 3,825,003 | 7/1974 | Kruck | 128/218 NV |

FOREIGN PATENT DOCUMENTS 836278  6/1960  United Kingdom ............. 128/218 NV

*Primary Examiner*—John D. Yasko
*Attorney, Agent, or Firm*—Lowe, Kokjer, Kircher, Wharton & Bowman

[57] ABSTRACT

A combination cap and needle unit permits a syringe tube to be capped for storage or prepared for use with the needle in operative position to inject fluid. The cap structure fits removably on the syringe tube and carries a rubber seal element that initially seals the tube outlet. The needle is connected integrally with the cap by a frangible heat seal which may be broken to release the needle so that it may be pierced through the rubber seal element.

4 Claims, 3 Drawing Figures

COMBINED CAP AND NEEDLE STRUCTURE

BACKGROUND AND SUMMARY OF THE INVENTION

This invention relates generally to syringes and deals more particularly with a combination cap and needle structure for a syringe.

At present, syringes are typically disposable units in the form of a syringe tube which may be used with either a cap or a needle. Liquid is drawn into the syringe tube and either the cap or needle is installed, depending on whether the syringe is to be temporarily stored or immediately put to use.

In situations where the syringe is to be stored for a time after being filled with fluid, it is necessary to fill it with fluid, cap it for storage, and then uncap it prior to finally installing the needle at the time of use. Aside from the obvious difficulty and time consumed by this cumbersome procedure, the needle must be temporarily stored apart from the syringe during the time the tube is capped. As a result, the needle is likely to be misplaced or, more importantly, to become contaminated or damaged in some other manner.

Consequently, there is a need for a syringe cap and needle structure which is constructed in a manner to avoid the foregoing problems. It is the principle goal in the present invention to meet that need.

More specifically, it is an object of the invention to provide a combined cap and needle structure for a syringe. Accordingly, even when the tube is capped, the needle is conveniently located on the syringe unit where it is readily available for use.

Another object of the invention is to provide a cap and needle structure of the character described which may be quickly and easily converted from a sealed condition to an operating condition wherein the needle is in place and ready for use to inject the liquid contained in the syringe tube. This important feature is accomplished by mounting the needle at a position wherein it may be quickly and easily forced through the seal element which serves to cap the syringe tube during storage.

A further object of the invention is to provide a cap and needle structure of the character described wherein the needle is accurately guided as it is moved in a manner to pierce the seal element.

An additional object of the invention is to provide a cap and needle structure of the character described wherein the needle is protected against contamination during storage. To this end, a protective needle guard completely covers the needle until removed immediately prior to use.

Yet another object of the invention is to provide a cap and need structure of the character described which is simple and economical to construct and use, which is well suited for mass production, and which is readily adapted for use with syringes of various types and sizes.

Other and further objects of the invention, together with the features of novelty appurtenant thereto, will appear in the course of the following description of the drawings.

DETAILED DESCRIPTION OF THE INVENTION

Figure 1:
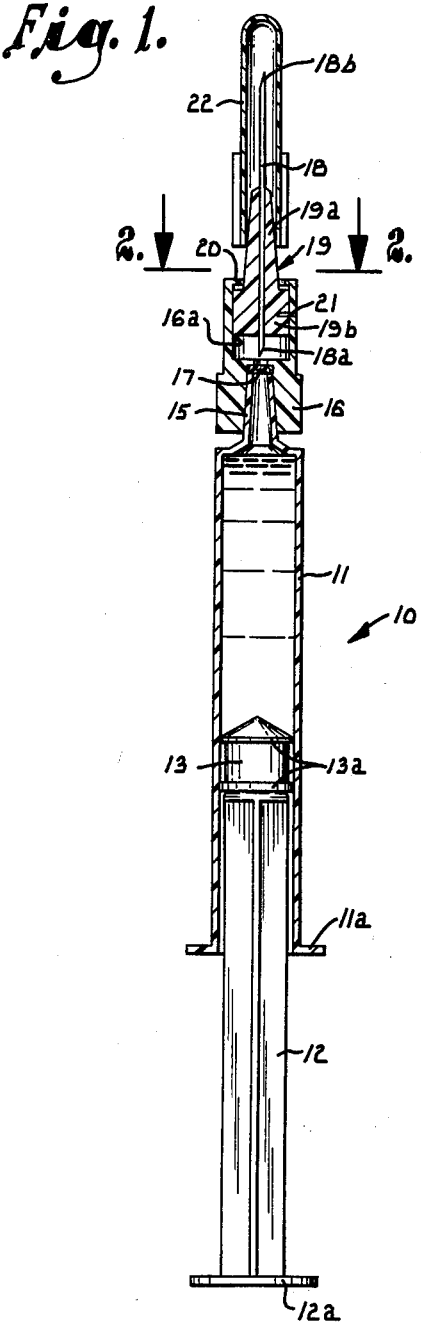
Figure 2:
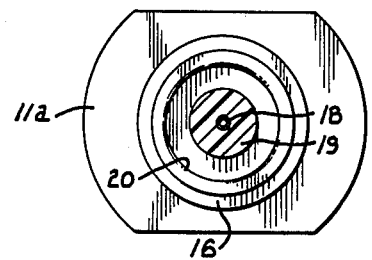
Figure 3:
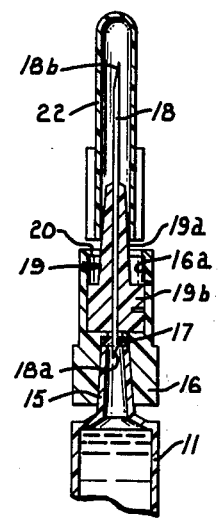

In the accompanying drawing which forms a part of the specification and is to be read in conjunction therewith, and in which like reference numerals are employed to indicate like parts in the various views:

FIG. 1 is a sectional view of a syringe provided with a combination cap and needle structure constructed according to a preferred embodiment of the present invention, with the syringe tube in the capped position;

FIG. 2 is an enlarged sectional view taken generally along line 2—2 of FIG. 1 in the direction of the arrows; and FIG. 3 is a fragmentary sectional view similar to FIG. 1 but showing the invention in the operating position wherein the seal is pierced by the needle. Referring now to the drawing in more detail and initially to FIG. 1, reference numeral 10 generally designates a conventional syringe of the type with which the cap and needle unit of the present invention may be used. The syringe 10 has the usual hollow plastic tube 11 having a large open end provided with a flange 11a. A plunger 12 extends through the open end of tube 11 and is able to slide axially therein. Plunger 12 likewise has a flange 12a at one end. The opposite end of the plunger carries a piston 13 which is constructed of rubber or another sealing material. The piston has rings 13a which fit tightly against the internal tube walls in order to effect a seal thereagainst. The discharge end of tube 11 is provided with an integral neck portion 15 which is reduced in size and which tapers toward its open end.

In accordance with the present invention, a cylindrical cap member 16 is constructed to fit closely but removably on the syringe tube neck 15. Cap 16 carries an internal rubber seal element 17 approximately halfway along its length which seats firmly over the discharge end of neck 15 when the cap is in place thereon. Above seal element 17, cap 16 has a large cylindrical bore 16a.

Cap member 16 is provided with a thin metal needle 18 which is carried on a guide member 19 having a tapered nose portion 19a and cylindrical base portion 19b that fits closely but slidably within the bore 16a of the cap. Needle 18 extends completely through guide member 19 and has a pointed inlet end 18a located immediately above seal element 17 within bore 16a. Needle 18 is hollow and thus presents a passage extending from the open inlet end 18a to the pointed tip 18b presented on the outer end of the needle and serving to inject the liquid contained in tube 11.

After the combined cap and needle unit has been assembled with member 19 installed in bore 16a, the upper rim of cap member 16 is heated to provide an enlarged ring 20 thereon which prevents member 19 from sliding out of bore 16a or otherwise slipping free of member 16. Guide member 19 is initially connected with cap 16 in frangible fashion by a penetrating heat seal which may be effected as indicated at 21 by inserting a heated pin or the like through the wall of cap 16 and into member 19. After the pin is withdrawn, it will have sealed members 16 and 19 together with a heat seal 21 which may be easily broken as will be explained in more detail.

Needle 18 is protected by a removable needle guard 22 which is of generally tubular form with a closed end. When installed on the syringe, the needle guard 22 completely encloses the needle and fits around a portion of the guide member nose 19a, as shown in FIG. 1.

In use, the syringe 10 is initially empty. The plunger 12 may be pulled to draw the desired amount of fluid into tube 11 through the open end of neck 15. Cap 16 is then installed on the neck as shown in FIG. 1 such that seal 17 seats firmly over the open end of the neck in order to cap the tube for temporary storage purposes.

When the syringe is to be used, it is necessary only to press firmly downwardly on the needle guard 22 with sufficient force to break the penetrating heat seal 21. When this occurs, guide 19 and needle 18 are disconnected from cap 16 so that continued pressure on needle guard 22 causes the pointed inlet end 18a of needle 18 to pierce through seal element 17. As this occurs, the close fit of guide member 19 in the guide channel provided by bore 16a restricts needle 18 to axial movement. When guide 19 reaches the end of bore 16a and comes into engagement with the shoulder there presented, needle 18 extends completely through seal 17, as shown in FIG. 3. In this position, the open inlet end 18a is in communication with the interior of tube 11 so that fluid may be forced through the needle and injected from tip 18b when plunger 12 is depressed. Of course, the needle guard 22 is removed immediately prior to use of the syringe.

It is contemplated that the syringe 10 will be discarded after being used once. It is pointed out that the needle 18 is completely enclosed at all times prior to use, and that the cooperation between guide member 19 and bore 16a assures that the inlet end 18a of the needle will completely pierce the seal element 17 in the manner intended. Further, the seal member 17 provides an effective cap for tube 11 prior to being pierced by the needle when the syringe is being prepared for use to inject the liquid.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be intepreted as illustrative and not in a limiting sense.

Having thus described the invention, I claim:

1. A combined cap and needle structure adapted for use with a syringe tube having a hollow body portion with a plunger end and a discharge end and a neck portion integrally formed with said body portion to provide a discharge opening at the discharge end of said body portion, said neck portion being of a reduced diameter and tapered to its discharge opening, said cap and needle structure comprising:
   a cap member having an opening defined therein, said opening being arranged to receive the neck portion of said syringe tube to removably install said cap member on the syringe tube;
   said cap member is also provided with a cylindrically shaped bore which is adjacent to said opening and interconnected with said opening by a hollow channel;
   a sealing member positioned within said opening between the discharge opening of the neck portion of said syringe tube and said hollow channel to substantially seal the discharge opening of said syringe from the passage of fluid;
   the needle having inlet and outlet ends with a passage extending between the inlet and outlet ends thereof;
   a guide member attached to a portion of said needle intermediate its inlet and outlet ends, said guide member having a cylindrically shaped base portion which fits slidably within the cylindrical shaped bore of said cap member to move the needle from a non-piercing position wherein the inlet end of said needle is in proximity to said sealing member to a piercing position wherein the inlet end of said needle passes through said sealing member into communication with the interior of said syringe tube; and
   a frangible heat seal connecting said guide member to said cap member in a non-piercing position, said frangible heat seal being adapted to be broken to permit movement of the needle to said piercing position.

2. The invention set forth in claim 1, including a removable needle guard for covering the outlet end of said needle.

3. The invention set forth in claim 1, including a ring at the end of said bore preventing removal of said guide portion therefrom.

4. The invention set forth in claim 1, wherein the inlet end of said needle is pointed to facilitate piercing of said sealing member.

* * * * *